United States Patent [19]

Hirai

[11] Patent Number: 4,492,794

[45] Date of Patent: Jan. 8, 1985

[54] 2-GUANIDINO-4-HYDROXYMETHYL-THIAZOLE AND DERIVATIVES THEREOF

[75] Inventor: Kentaro Hirai, Kyoto, Japan

[73] Assignee: Shionogi & Co., Ltd., Osaka, Japan

[21] Appl. No.: 488,821

[22] Filed: Apr. 26, 1983

[30] Foreign Application Priority Data

Oct. 27, 1981 [JP] Japan .................................. 56/172391

[51] Int. Cl.³ .......................................... C07D 277/38
[52] U.S. Cl. .................... 548/193; 548/194; 424/270
[58] Field of Search ................................. 548/193, 194

[56] References Cited

U.S. PATENT DOCUMENTS 4,347,370  8/1982  Gilman ................................ 548/193
4,362,736 12/1982  Hirata ................................ 424/270

Primary Examiner—Robert Gerstl
Attorney, Agent, or Firm—Birch, Stewart, Kolasch & Birch

[57] ABSTRACT

A compound of the formula:

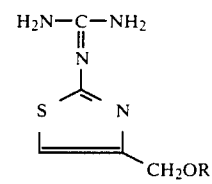

wherein R is hydrogen, $C_1$-$C_5$ alkanoyl or substituted sulfonyl, which is useful as a synthetic intermediate to 2-guanidino-4-[2-(formamido)ethylthiomethyl]thiazole, histamine $H_2$ receptor antagonist.

10 Claims, No Drawings

2-GUANIDINO-4-HYDROXYMETHYLTHIAZOLE AND DERIVATIVES THEREOF

The present invention relates to 2-guanidino-4-hydroxymethylthiazole and derivatives thereof. More particularly, this invention relates to a compound of the formula:

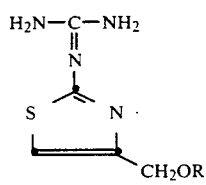

in which R is hydrogen, $C_1$-$C_5$ alkanoyl or substituted sulfonyl, which is useful as a synthetic intermediate to 2-guanidino-4-[2-(formamido)ethylthiomethyl]thiazole, histamine $H_2$ receptor antagonist. [U.S. patent application Ser. No. 256,918].

In the formula (I), the $C_1$-$C_5$ alkanoyl includes illustratively formyl, acetyl, propionyl, butyryl and valeryl, with the acetyl group being preferred. The substituted sulfonyl includes illustratively $C_1$-$C_5$ alkanesulfonyl such as methanesulfonyl, ethanesulfonyl, propanesulfonyl, butanesulfonyl and pentanesulfonyl, preferably methanesulfonyl (mesyl) and $C_6$-$C_8$ arenesulfonyl such as benzenesulfonyl, toluenesulfonyl, or xylenesulfonyl, preferably 4-toluenesulfonyl (tosyl).

Said compound of the formula (I) can be prepared by the following scheme:

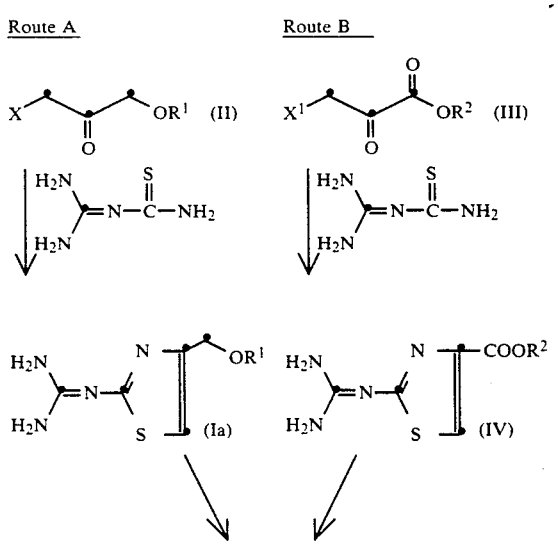

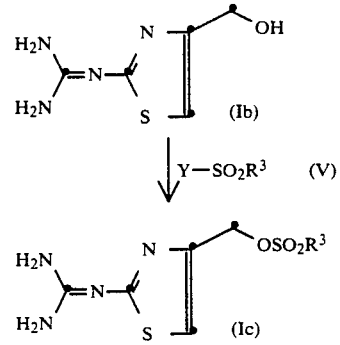

(in which $R^1$ is $C_1$-$C_5$ alkanoyl, $R^2$ is $C_1$-$C_5$ alkyl, $R^3$ is $C_1$-$C_5$ alkyl or $C_6$-$C_8$ aryl, and X, $X^1$ and Y are each halogen (e.g. chlorine, bromine, etc.)).

Route A

2-Guanidino-4-(alkanoyloxymethyl)thiazole (Ia) is prepared by reacting 1-alkanoyloxy-3-halo-2-propanone (II) with guanylthiourea in an inert solvent such as acetone, dimethylformamide, dimethylsulfoxide, or pyridine. The reaction may be performed at room temperature or under heating up to 100° C., preferably 20° to 70° C.

Then the above product (Ia) is subjected to hydrolysis with an inorganic base such as an alkali metal hydroxide (e.g. sodium hydroxide, potassium hydroxide), alkali an metal hydrogencarbonate (e.g. potassium hydrogencarbonate, sodium hydrogencarbonate) or an alkali metal carbonate (e.g. potassium carbonate, sodium carbonate). The reaction may be performed at room temperature (about 15° to 20° C.) or under heating up to 100° C. in a solvent such as methanol, ethanol, dioxane, acetone, dimethylsulfoxide or water or a mixed solvent thereof. Thus 2-guanidino-4-hydroxymethylthiazole (Ib) is prepared in a good yield.

The starting 1-alkanoyloxy-3-halo-2-propanone (II) is prepared by reacting epihalohydrin with an alkanoic acid to give 1-alkanoyloxy-3-halo-2-propanol and oxidizing the resulting propanol with a Jones reagent.

Route B

2-Guanidino-4-alkoxycarbonylthiazole (IV) is prepared by reacting alkyl 3-halopyruvate (III) with guanylthiourea in a solvent. The reaction is performed under heating about 50° to 120° C., preferably about 65° to 95° C. in a solvent such as methanol, ethanol, dimethylformamide, dimethylsulfoxide, pyridine or hexamethylphosphoric triamide.

Then the above product (IV) is reduced with an aluminum hydride compound such as lithium aluminum hydride, sodium bis(methoxyethoxy)aluminum hydride, lithium bis(methoxyethoxy)aluminum hydride or the like. The reaction is performed at room temperature to the boiling point of the solvent used in an appropriate solvent such as tetrahydrofuran, dioxane, diglyme, toluene or the like. Thus 2-guanidino-4-hydroxymethylthiazole (Ib) is prepared in a good yield.

The above product (Ib) is converted into 2-guanidino-4-(substituted sulfonyloxymethyl)thiazole (Ic) by reacting the compound (Ib) with an alkanesulfonyl or arenesulfonyl halide (V) in the presence of a base such as pyridine or triethylamine. The reaction may be performed in a solvent such as acetone, toluene, dimethylformamide, dimethylsulfoxide, or hexamethylphosphoric triamide at room temperature.

The product (I), namely 2-guanidino-4-hydroxymethylthiazole (Ib) and derivatives thereof (Ia) and (Ic) are useful as synthetic intermediates to 2-guanidino-4-[2-(formamido)ethylthiomethyl]thiazole, histamine $H_2$ receptor antagonist [U.S.patent application Ser. No. 256,918]. For example, said $H_2$ antagonist is prepared by reacting 2-guanidino-4-hydroxymethylthiazole (Ib) with N,N'-diformylcystamine in the presence of a phosphorus compound such as tributylphosphine, triphenylphosphine or methylphenylaminotriphenylphosphonium iodide [J.Org.Chem., 28, 483 (1963)]. This reaction may be performed under cooling or heating (0° to 100° C.), preferably at room temperature in a protic solvent such as pyridine, dimethylformamide or the like.

Presently preferred and practical embodiments of the present invention are illustratively shown in the following examples.

EXAMPLE 1

Preparation of 2-guanidino-4-acetoxymethylthiazole hydrochloride:

(1) A suspension of epichlorhydrin (27.8 g) and sodium acetate (12.3 g) in acetic acid (36 g) is heated at 50°–55° C. for 8 hours. The reaction mixture is allowed to stand overnight and concentrated in vacuum. The residue is neutralized with aqueous sodium hydrogencarbonate and shaken with ether. The ethereal layer is dried over anhydrous sodium sulfate and concentrated in vacuum. The residue is distilled in vacuum to give 1-acetoxy-3-chloro-2-propanol (30 g) as an oil boiling at 115°–116° C./13 mm Hg. The yield is 65.4%.

(2) To a solution of 1-acetoxy-3-chloro-2-propanol (15.3 g) in acetone (250 ml) is dropwise added Jones reagent (37.4 ml) containing chromic anhydride (10.39 g) and conc. sulfuric acid (10.18 ml) in 1 hour, and the resultant mixture is stirred at room temperature for 3 hours. The reaction mixture is mixed with isopropanol (10 ml) and the insoluble material is filtered off. The organic layer is concentrated in vacuum, and the residue is distilled to give 1-acetoxy-3-chloro-2-propanone (9 g) as an oil boiling at 102°–104° C./15 mm Hg. The yield is 60.0%.

NMR (CDCl$_3$), $\delta$2.17 (s, 3H), 4.13 (s, 2H), 4.87 (s, 2H).

[Heese, et al., Ber. 48, 1986 (1915)].

(3) A suspension of 1-acetoxy-3-chloro-2-propanone (4.52 g) and guanylthiourea (3.55 g) in acetone (100 ml) is stirred at room temperature for 64 hours. The precipitated crystals are filtered to give 2-guanidino-4-acetoxymethylthiazole hydrochloride hemihydrate (6.2 g) as crystals melting at 170°–172° C.

EXAMPLE 2

Preparation of 2-guanidino-4-hydroxymethylthiazole:

(1) A suspension of guanylthiourea (2.36 g) and ethyl 3-bromopyruvate (4.8 g) in dry ethanol (50 ml) is refluxed under stirring for 2.5 hours. The reaction mixture is concentrated in vacuum to dryness, and the residue is dissolved in water (about 100 ml). The aqueous solution is washed with ethyl acetate and made alkaline with 5% sodium hydrogencarbonate solution. The precipitated crystals are filtered, washed with water and dried to give 2-guanidino-4-ethoxycarbonylthiazole (3.6 g) as crystals. The yield is 84%.

NMR (d$_6$-DMSO), $\delta$1.28 (t, 3H, J=7 Hz), 4.23 (q, 2H, J=7 Hz), 6.93 (br. s, 4H), 7.55 (s, 1H).

(2) To a suspension of lithium aluminum hydride (0.5 g) in dry tetrahydrofuran (260 ml) is portionwise added 2-guanidino-4-ethoxycarbonylthiazole (3.6 g) at 0° C. with stirring in half an hour, and the resultant mixture is refluxed under stirring for 4 hours. Ethyl acetate and water are added to the reaction mixture for decomposing excess lithium aluminum hydride. The organic layer is separated and the residual layer is extracted with methanol. The methanolic extract is combined with the organic layer, dried over anhydrous sodium sulfate and concentrated in vacuum. The residue is chromatographed on a column of silica gel, which is eluted with ethyl acetate:methanol (4:1, v/v). The eluate is concentrated in vacuum to give 2-guanidino-4-hydroxymethylthiazole (1.8 g) as crystals melting at 163°–165° C. The yield is 62.2%.

NMR (CD$_3$OD), $\delta$4.48 (s, 2H), 6.57 (s, 1H).

EXAMPLE 3

Preparation of 4-guanidino-2-hydroxymethylthiazole:

To a solution of sodium hydroxide (2 g) in methanol (100 ml) is added 2-guanidino-4-acetoxymethylthiazole hydrochloride hemihydrate (6.15 g), and the resultant mixture is stirred at room temperature for half an hour. The insoluble material is filtered off, and the filtrate is concentrated in vacuum. The residue is chromatographed on a column of silica gel, which is eluted with methanol:ethyl acetate (1:4, v/v). The eluate is concentrated to give 2-guanidino-4-hydroxymethylthiazole (3.5 g) as crystals melting at 163° to 165° C. The yield is 82.9%.

Anal. Calcd. for C$_5$H$_8$N$_4$OS: C, 34.87; H, 4.68; N, 32.54; S, 18.62 (%). Found: C, 34.88; H, 4.58; N, 32.13; S, 18.51 (%).

EXAMPLE 4

Preparation of 2-guanidino-4-hydroxymethylthiazole:

Using potassium carbonate (6.6 g) and methanol (90 ml), the reaction is performed as in Example 3, whereby 2-guanidino-4-hydroxymethylthiazole (7.2 g) is obtained from 2-quanidino-4-acetoxymethylthiazole hydrochloride hemihydrate (12.4 g). The yield is 87.2%.

EXAMPLE 5

Preparation of 2-guanidino-4-(4-toluenesulfonyloxymethyl)thiazole:

To a solution of 2-guanidino-4-hydroxymethylthiazole (0.69 g) in pyridine (5 ml) is gradually added 4-toluenesulfonyl chloride (0.763 g), and the resultant mixture is stirred at room temperature for 4 hours. The resultant mixture is concentrated in vacuum, and the residue is chromatographed on a column of silica gel, which is eluted with methanol. The eluate is concentrated in vacuum to give 2-guanidino-4-(4-toluenesulfonyloxymethyl)thiazole (0.6 g) as an oil. The yield is 45.8%.

NMR (CD$_3$OD), $\delta$2.33 (s, 3H), 5.87 (s, 2H), 7.62 (s, 1H), 7.17–7.66 (ABq, J=8 Hz, 4H), IR $\nu_{max}^{film}$ 1170, 1220 cm$^{-1}$.

EXAMPLE 6

To a solution of 2-guanidino-4-hydroxymethylthiazole (0.86 g) in pyridine (6 ml) is gradually added methanesulfonyl chloride (0.6 g) under ice cooling, and the resultant mixture is stirred at room temperature for 2 hours. The reaction mixture is concentrated in vacuum, and the residual oil is chromatographed on a column of silica gel, which is eluted with methanol. The eluate is concentrated in vacuum to give 2-guanidino-4-(methanesulfonyloxymethyl)thiazole (1.2 g) as an oil. The yield is 96%.

NMR (CD$_3$OD), δ2.70 (s, 3H), 5.83 (s, 2H), 7.57 (s, 1H).

IR $\nu_{max}^{film}$ 1170, 1220 cm$^{-1}$.

REFERENTIAL EXAMPLE

A mixture of 2-guanidino-4-hydroxymethylthiazole (0.517 g), N,N'-diformylcystamine (1.87 g), tributylphosphine (1.82 g) and pyridine (1.5 ml) is stirred at room temperature for 8 hours. The reaction mixture is allowed to stand overnight and concentrated in vacuum and treated with maleic acid. The residue is chromatographed on a column of silica gel, which is eluted with methanol:ethyl acetate (1:4, v/v). The eluate is concentrated in vacuum to give 2-guanidino-4-[2-(formamido)ethylthiomethyl]thiazole maleate (0.81 g) as crystals melting at 146°-148° C. The yield is 71.7%.

What I claim is:

1. A compound of the formula:

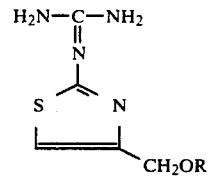

wherein R is hydrogen, C$_1$-C$_5$ alkanoyl, C$_1$-C$_5$ alkanesulfonyl or C$_6$-C$_8$ arenesulfonyl.

2. A compound according to claim 1, in which R is hydrogen.

3. A compound according to claim 1, in which R is C$_1$-C$_5$ alkanoyl.

4. A compound according to claim 3, in which R is acetyl.

5. A compound according to claim 1, in which R is C$_1$-C$_5$ alkanesulfonyl.

6. A compound according to claim 5, in which R is methanesulfonyl.

7. A compound according to claim 1, in which R is C$_6$-C$_8$ arenesulfonyl.

8. A compound according to claim 7, in which R is toluenesulfonyl.

9. A compound according to claim 8, in which the toluenesulfonyl is 4-toluenesulfonyl.

10. A compound according to claim 1, in which said C$_6$-C$_8$ arenesulfonyl is benzenesulfonyl, toluenesulfonyl or xylenesulfonyl.